United States Patent
Muehlberg et al.

(10) Patent No.: US 12,002,582 B2
(45) Date of Patent: Jun. 4, 2024

(54) METHOD FOR OBTAINING DISEASE-RELATED CLINICAL INFORMATION

(71) Applicant: Siemens Healthcare GmbH, Erlangen (DE)

(72) Inventors: Alexander Muehlberg, Nuremberg (DE); Oliver Taubmann, Weilersbach (DE); Alexander Katzmann, Fuerth (DE); Michael Suehling, Erlangen (DE)

(73) Assignee: Siemens Healthineers AG, Forchheim (DE)

( * ) Notice: Subject to any disclaimer, the term of this patent is extended or adjusted under 35 U.S.C. 154(b) by 544 days.

(21) Appl. No.: 17/109,332

(22) Filed: Dec. 2, 2020

(65) Prior Publication Data
US 2021/0183514 A1  Jun. 17, 2021

(30) Foreign Application Priority Data
Dec. 12, 2019  (EP) .................................... 19215716

(51) Int. Cl.
G16H 50/20        (2018.01)
A61B 6/00         (2006.01)
(Continued)

(52) U.S. Cl.
CPC ............. G16H 50/20 (2018.01); A61B 6/032 (2013.01); A61B 6/5217 (2013.01);
(Continued)

(58) Field of Classification Search
CPC ........ G16H 30/40; G16H 50/20; G16H 50/30; G16H 50/70; G16H 20/00
See application file for complete search history.

(56) References Cited

U.S. PATENT DOCUMENTS

2010/0057651 A1   3/2010  Dehing-Oberije et al.
2020/0085382 A1*  3/2020  Taerum ................ G06V 10/764
(Continued)

FOREIGN PATENT DOCUMENTS

| EP | 3792871 A1 | 3/2021 | |
| WO | WO-2008035286 A2 * | 3/2008 | ........... A61B 6/5217 |
| WO | WO-2020257482 A1 * | 12/2020 | ........... A61B 5/0035 |

OTHER PUBLICATIONS

Sinke, Michel RT, et al. "Bayesian exponential random graph modeling of whole-brain structural networks across lifespan." NeuroImage 135 (2016): 79-91. (Year: 2016).*

(Continued)

*Primary Examiner* — Jason B Dunham
*Assistant Examiner* — Constantine Siozopoulos
(74) *Attorney, Agent, or Firm* — Harness, Dickey & Pierce, P.L.C.

(57) ABSTRACT

A computer-implemented method is for providing a clinical information. In an embodiment, the computer-implemented method includes receiving input data including a graph representation of a plurality of disease lesions of a patient; applying a trained function to the input data to generate the clinical information, the trained function being based on a graph machine learning model; and providing the clinical information, the clinical information including at least one information for prediction of the disease progression, survival or therapy response of the patient.

21 Claims, 4 Drawing Sheets

(51) Int. Cl.
| | |
|---|---|
| A61B 6/03 | (2006.01) |
| G06T 7/00 | (2017.01) |
| G16H 15/00 | (2018.01) |
| G16H 30/20 | (2018.01) |
| G16H 30/40 | (2018.01) |
| G16H 50/50 | (2018.01) |
| G16H 50/70 | (2018.01) |
| G16H 70/60 | (2018.01) |

(52) U.S. Cl.
CPC ........... G06T 7/0016 (2013.01); G16H 15/00 (2018.01); G16H 30/20 (2018.01); G16H 30/40 (2018.01); G16H 50/50 (2018.01); G16H 50/70 (2018.01); G16H 70/60 (2018.01); *G06T 2200/24* (2013.01); *G06T 2207/20081* (2013.01); *G06T 2207/30096* (2013.01)

(56) References Cited

U.S. PATENT DOCUMENTS

| | | | |
|---|---|---|---|
| 2020/0211694 A1* | 7/2020 | Nye | ........................... G06T 7/11 |
| 2021/0082569 A1 | 3/2021 | Muehlberg et al. | |

OTHER PUBLICATIONS

Keshavamurthy, Krishna N., et al. "Machine learning algorithm for automatic detection of CT-identifiable hyperdense lesions associated with traumatic brain injury." Medical Imaging 2017: Computer-Aided Diagnosis. vol. 10134. SPIE, 2017. (Year: 2017).*

Bronstein, M. et. al., "Geometric deep learning: going beyond Euclidean data", IEEE Signal Processing Magazine, 2017.

Tobias Skovgaard Jepsen: "How to do Deep Learning on Graphs with Graph Convolutional Networks"; Sep. 8, 2018 (Sep. 18, 2018), XP055689132, Retrieved from the Internet: URL:https://towardsdatascience.com/how-todo-deep-learning-on-graphs-with-graph-convolutional-networks-7d2250723780;.

Kung-Hsiang et al: "A Gentle Introduction 1-17 to Graph Neural Networks (Basics, DeepWalk, and GraphSage)" Feb. 10, 2019 (Feb. 10, 2019), XP055689130, Retrieved from the Internet: URL:https://towardsdatascience.com/a-gentle-introduction-to-graph-neural-network-basics-deepwalk-and-graphsage-db5d540d50b3.

Kipf, Thomas N., et al., "semi-supervised classification with graph convolutional networks", ICLR 2017, XP55457092A, Feb. 22, 2017; 2017.

Shrey Gadiya et al: "Histographs: in Histopathology" ,arxiv.org, Cornell University Library, 201 Olin Library Cornell University Ithaca, NY 14853, Aug. 14, 2019 (Aug. 14, 2019), XP081462232.

Hansen, L. et. al., "Sparse Structured Prediction for Semantic Edge Detection in Medical Images", MIDL, 2019.

Aoki, T. et. al., "Peripheral lung adenocarcinoma: correlation of thin-section CT findings with histologic prognostic factors and survival", Radiology, 220(3), pp. 803-809, 2001.

Sasaki, K. et al., "The tumor burden score: a new "metro-ticket" prognostic tool for colorectal liver metastases based on tumor size and number of tumors", Annals of surgery 267.1, pp. 132-141, 2018.

Etchebehere, Elba C. et al. "Prognostic Factors in Patients Treated with 223Ra: The Role of Skeletal Tumor Burden on Baseline 18F-Fluoride PET/CT in Predicting Overall Survival" Journal of Nuclear Medicine, vol. 56, No. 8, pp. 1177-1184, 2015.

* cited by examiner

METHOD FOR OBTAINING DISEASE-RELATED CLINICAL INFORMATION

PRIORITY STATEMENT

The present application hereby claims priority under 35 U.S.C. § 119 to European patent application number EP19215716.2 filed Dec. 12, 2019, the entire contents of which are hereby incorporated herein by reference.

FIELD

Example embodiments of the application generally invention are generally in the field of medical imaging and medical image analysis.

BACKGROUND

Medical imaging can be performed with a variety of imaging modalities such as X-ray, ultrasound, magnetic resonance imaging (MRI), computed tomography (CT), positron-emission tomography (PET), single-photon emission computed tomography (SPECT) etc. as are known in the art. The imaging is performed with a respective imaging device, also referred to as "scanner".

The spatial distribution of disease lesions of multi-focal diseases is a predictive factor for evaluating the prognosis and therapy response for such diseases.

A well-known example for such multi-focal diseases are tumor diseases. In tumor diseases information about the primarius also known as primary tumor and metastases is an important predictive factor for disease survival and therapy response. Both global features (e.g. spatial position and relationship of primarius and metastases) and local features (e.g. parameters such as size, volume, texture, etc. of the primarius or individual metastases) are predictive factors. The primarius and the metastasis are subsequently called tumor lesions.

With more than 1,800,000 cases and nearly 862,000 deaths per year, metastatic colorectal cancer (mCRC) is one of the leading causes of cancer related deaths in modern societies. An adequate and early assessment is systematically correlated with a significantly improved overall patient survival and patient wellbeing. Within tumor therapy, the approximated patient survival itself is an important variable for therapy adjustment, e.g. by adapting the medication, or escalating and deescalating the therapy. Thus, it contributes to an overall better patient care and patient survival. However, currently there is no established and generally accepted technique to quantitatively estimate patient survival, meaning that this estimation largely builds upon radiologic and oncologic experience. Hence, currently the quality of the estimation or prediction, respectively, of the patient survival time depends on the expertise of the radiologist or oncologist.

When looking at past efforts within medical imaging, researchers and clinicians have focused their resources on estimating the survival of patients based on features like volume (Etchebehere et al., 2015) or maximum diameter (Aoki et al., 2001) of a single tumor lesion, or the sum of these values for multiple tumor lesions (RECIST). These approaches assess the biology of single tumor lesions, which are important hints about the response to an intervention such as radiation therapy or chemotherapy. As this approach uses characteristics such as size or volume of selected single tumor lesions, we may say it uses local characteristics of individual lesions.

Furthermore, the anatomical tumor spread which relates to spatial characteristics of the spatial tumor lesion distribution is also predictive for survival and therapy response. As this approach uses characteristics such as distances and orientation of tumor lesions to each other we may say it relates to a global spatial distribution.

It is desirable to have a biomarker system that combines the two clinical research paths as defined above. Biomarkers are measurable indicators of biological states or conditions of an object of interest depicted in an input image. These types of problems are suitable for analysis with artificial intelligence, e.g. machine learning or deep learning. However, when choosing the complete image volume covering all tumor lesions as model input, this will typically lead to poor performance in practice given the enormous input space dimensionality. Therefore, an advanced system that would allow a holistic approach to analyze global and local characteristics needs a smart data representation and suitable deep learning algorithm.

Also, the distribution of tumors over different organs, i.e. the full-body tumor burden of a patient, cannot trivially be analyzed by conventional deep learning (DL) systems. This is not only due to an even larger input space dimensionality but also missing image information between image patches, e.g. if a patient has tumors of lung and liver, the regions in between are not always available as image data.

Further multi-focal diseases of high interest are chronical obstructive pulmonary diseases (COPD). The same embodiments and aspects as mentioned above for tumor diseases with regard to the plurality of tumor lesions can be observed in COPD with regard to panlobular emphysema or changes in the lung structure, which are indicative for pulmonary hypertension.

In a more general embodiment, the same observations hold true for any multi-focal disease. Other multi-focal diseases are e.g. inflammatory diseases (e.g. rheumatoid arthritis), degenerative diseases (e.g. Alzheimer), skin diseases, arterio-sclerotic diseases etc.

SUMMARY

A problem to be improved upon or even solved by at least one embodiment of the invention provides an advanced prediction system to estimate or predict, respectively, the disease progression, patient survival or therapy response with respect to multi-focal diseases.

In the following, embodiments of the invention are described with respect to the claimed systems as well as with respect to the claimed methods. Features, advantages or alternative embodiments herein can be assigned to the other claimed objects and vice versa. In other words, claims for the systems can be improved with features described or claimed in the context of the methods. In this case, the functional features of the method are embodied by objective units of the system.

Unless defined otherwise, technical and scientific terms used herein have the same meaning as commonly understood by one of ordinary skill in the art to which this invention belongs.

Furthermore, in the following embodiments of the invention are described with respect to methods and systems for providing clinical information related to any multi-focal disease as well as with respect to methods and systems for training a trained function for providing the clinical information. Features, advantages or alternative embodiments herein can be assigned to the other claimed objects and vice versa. In other words, claims for methods and systems for training the trained function for providing the clinical information can be improved with features described or claimed in context of the methods and systems for providing the clinical information, and vice versa.

At least one embodiment of the invention relates to a computer-implemented method providing a clinical information, comprising receiving input data, wherein the input data comprises a graph representation of a plurality of disease lesions of a patient, applying a trained function to the input data to generate the clinical information, wherein the trained function is based on a graph machine learning model, and providing the clinical information, wherein the clinical information comprises at least one information for the prediction of the disease progression, the survival, or therapy response of the patient.

In a further embodiment, the invention relates to a system for providing the clinical information, comprising a first interface, configured for receiving input data, wherein the input data comprises a graph representation of a plurality of disease lesions of a patient, comprising a second interface, configured for providing the clinical information, wherein the clinical information comprises at least one information for the prediction of the disease progression, the survival, or the therapy response of the patient and comprising a computation unit, configured for applying a trained function to the input data to generate the clinical information, wherein the trained function is based on a graph machine learning model, wherein the information is generated.

In a further embodiment, the invention relates to a computer program comprising instructions which, when the program is executed by a computer system, cause the computer system to carry out the method of at least one embodiment of the invention as explained above together with its potential aspects.

In a further embodiment, the invention relates to a computer-readable medium comprising instructions which, when executed by a computer system, cause the computer system to carry out the method of at least one embodiment of the invention explained above together with its potential aspects.

In a further embodiment, the invention relates to a training system, comprising a first training interface, configured for receiving input training data, wherein the input training data comprises a graph representation of a plurality of disease lesions of a patient, a second training interface, configured for receiving output training data, wherein the input training data is related to the output training data, wherein the output draining data comprises a clinical information, wherein the clinical information comprises at least one information for the prediction of the disease progression, the survival or therapy response of the patient, a training computation unit, configured for training a function based on the input training data and the output training data, a third training interface, configured for providing the trained function.

In a further embodiment, the invention relates to a computer program comprising instructions which, when the program is executed by a training system, cause the training system to carry out the method of at least one embodiment, together with its potential aspects and embodiments.

In a further embodiment, the invention relates to a computer-readable medium comprising instructions which, when executed by a training system, cause the training system to carry out the method of at least one embodiment, together with its potential aspects and embodiments.

In a further embodiment, the invention relates to a computer-implemented method for providing a clinical information, comprising:

receiving input data, the input data including a graph representation of a plurality of disease lesions of a patient;

applying a trained function to the input data to generate the clinical information, the trained function being based on a graph machine learning model; and providing the clinical information, the clinical information including at least one information for prediction of disease progression, survival, or therapy response of the patient.

In a further embodiment, the invention relates to a system for providing a clinical information, comprising:

a first interface, configured to receive input data, the input data including a graph representation of a plurality of disease lesions of a patient;

a second interface, configured to provide the clinical information, the clinical information including at least one information for prediction of disease progression, survival, or therapy response of the patient; and at least one processor, configured to apply a trained function to the input data, to generate the clinical information, the trained function being based on a graph machine learning model.

In a further embodiment, the invention relates to a non-transitory computer program product, storing a program including instructions which, when the program is executed by a computer system, cause the computer system to carry out the method of an embodiment.

In a further embodiment, the invention relates to a non-transitory computer-readable medium storing instructions which, when executed by a computer system, cause the computer system to carry out the method of an embodiment.

In a further embodiment, the invention relates to a training system, comprising a first training interface, configured to receive input training data, the input training data including a graph representation of a plurality of disease lesions of a patient;

a second training interface, configured to receive output training data, the input training data being related to the output training data and the output training data including a clinical information, the clinical information including at least one information for prediction of disease progression, survival, or therapy response of the patient;

at least one processor, configured to train a function based on the input training data and the output training data; and a third training interface, configured to provide the trained function.

BRIEF DESCRIPTION OF THE DRAWINGS

The present invention and its technical field are subsequently explained in further detail by example embodiments shown in the drawings. The example embodiments only conduce better understanding of the present invention and in no case are to be construed as limiting for the scope of the present invention. Particularly, it is possible to extract aspects of the subject-matter described in the figures and to combine it with other components and findings of the present description or figures, if not explicitly described differently. Equal reference signs refer to the same objects, such that explanations from other figures may be supplementary used.

DETAILED DESCRIPTION OF THE EXAMPLE EMBODIMENTS

Figure 1:
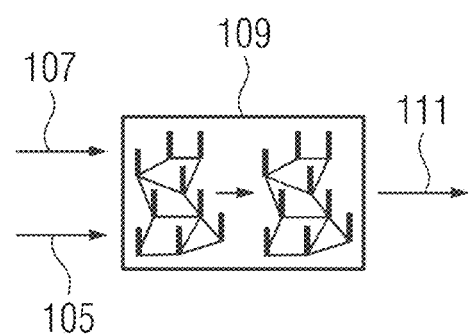
FIG. 1 shows a schematic flow chart of the method for providing a clinical information.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. The present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuity such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion.

In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

In particular, the trained function of the methods and systems for providing the clinical information can be adapted by the methods and systems for training the trained function for providing the clinical information. Furthermore, the input data can comprise advantageous features and embodiments of the training input data, and vice versa. Furthermore, the output data can comprise advantageous features and embodiments of the output training data, and vice versa.

In general, a trained function mimics cognitive functions that humans associate with other human minds. In particular, by training based on training data the trained function is able to adapt to new circumstances and to detect and extrapolate patterns.

In general, parameters of a trained function can be adapted by way of training. In particular, supervised training, semi-supervised training, unsupervised training, reinforcement learning and/or active learning can be used. Furthermore, representation learning (an alternative term is "feature learning") can be used. In particular, the parameters of the trained functions can be adapted iteratively by several steps of training.

In particular, a trained function can comprise a neural network, a support vector machine, a decision tree and/or a Bayesian network, and/or the trained function can be based on k-means clustering, Q-learning, genetic algorithms and/or association rules. In particular, a neural network can be a deep neural network, a convolutional neural network, a convolutional deep neural network or a graph machine learning model. Furthermore, a neural network can be an adversarial network, a deep adversarial network and/or a generative adversarial network.

In particular, a convolutional neural network is a deep learning neural network frequently applied in image analysis. It comprises at least an input layer, at least one convolutional layer, at least one pooling layer, at least one fully connected layer and an output layer. The order of the layers can be chosen arbitrarily, usually fully connected layers are used as the last layers before the output layer.

At least one embodiment of the invention relates to a computer-implemented method providing a clinical information, comprising receiving input data, wherein the input data comprises a graph representation of a plurality of disease lesions of a patient, applying a trained function to the input data to generate the clinical information, wherein the trained function is based on a graph machine learning model, and providing the clinical information, wherein the clinical information comprises at least one information for the prediction of the disease progression, the survival, or therapy response of the patient.

The term "prediction of the disease progression, the survival, or therapy response" of a patient, as used here-in, is meant to include both a prediction of an outcome of a patient undergoing a given therapy and a prognosis of a patient who is not treated. The term "prediction of the disease progression, the survival, or therapy response" may, in particular, relate to the probability of a patient undergoing an event, such as, but not limited to, disease-free survival, progression free survival, remission, occurrence of disease progression, occurrence of spread of disease lesions (e.g. metastasis) or occurrence of death, preferably within a given time frame.

The at least one information for the prediction of the disease progression, the survival or therapy response of the patient can comprise a qualitative information and/or a quantitative information, such as a score.

The term "therapy response" of a patient, as used herein, relates to the effectiveness of a certain therapy in a patient, meaning an improvement in any measure of patient status, including those measures ordinarily used in the art, such as overall survival, progression free survival, recurrence-free survival, and the like.

A graph machine learning model is a model trained by machine learning, which generally uses data represented in the form of graphs as input data or, generally speaking, uses machine learning based on graphs or a graph representation.

The input data comprising the graph representation of the plurality of disease lesions of the patient can be provided in any suitable form to which the trained function based on a graph machine learning model can be applied. In particular, and as an example, the graph representation can be expressed in the form of matrices encoding an information of the graph representation. In other words, the graph representation does not need to be displayed visually in the form of a graph. Alternatively, the graph representation can be a conventional graph within a coordinate system encoding the plurality of disease lesions and their information.

In particular, at least part of the input data can be derived from imaging data of a region of interest of the patient's anatomy. Imaging data can comprise raw data, a reconstructed image and/or a mathematical or data-based representation of an image.

According to an example embodiment of the invention, the graph representation of the plurality of disease lesions can comprise disease lesions which can be spread over a patient's body.

According to an alternative example embodiment of the invention, the graph representation of the plurality of disease lesions can comprise disease lesions which can be spread over several organs.

For these purposes, it is not necessary to have medical images of the body parts in between the different disease lesions. In other words, the body parts in between the disease lesions can be excluded by the graph representation of the plurality of disease lesions without losing information. In other words, the body parts in between the single disease lesions are not necessary for providing the clinical information. The body parts in between the single disease lesions contain unrelated information for disease diagnosis. That means that it is sufficient to have a plurality of image patches comprising each disease lesion at least once.

According to a further alternative example embodiment of the invention, the graph representation of the plurality of disease lesions can comprise disease lesions which can be spread over one particular organ (e.g. tumor lesions only in the liver, or COPD lesions only in the lung).

The clinical information can be any clinical information related to any multi-focal disease. The clinical information can be any information that can be used by a physician to decide about further therapy or palliative care of the patient.

According to an example embodiment of the invention, the disease can be a tumor disease and the plurality of disease lesions can be a plurality of tumor lesions. In particular, the plurality of tumor lesions can include the primarius, also called the primary tumor, and/or the metastases.

According to a further example embodiment of the invention, the plurality of disease lesions can be a plurality of lesions indicating a COPD. In this case the plurality of disease lesions can in particular comprise panlobular emphysema or changes in the lung structure, which are indicative for pulmonary hypertension.

According to an example embodiment of the invention, the graph machine learning model is a graph neural network, especially a graph convolutional neural network. According to a further example aspect of this embodiment of the invention, the graph machine learning model is trained by supervised training.

Encoding a plurality of disease lesions by a graph representation is useful for further analysis of the clinical-related predictive factors. This graph representation can serve as input for a graph machine learning model. By encoding the plurality of disease lesions by a graph representation missing images in between single disease lesions of the plurality of disease lesions are not a problem. The graph representation does not need any information about the body parts in between the single disease lesions. Hence, the full-body disease burden of a patient can be analyzed by the graph machine learning model without the necessity of having a complete medical image of the whole patient or at least of the whole body part which is affected by the disease lesions. The efficiency of the calculation of the clinical information can be optimized by encoding the plurality of disease lesions by a graph representation because the unnecessary information which is included in medical images is not encoded in the graph representation. Unnecessary information is for example information of the body parts in between single disease lesions and/or further information that is comprised in medical images in addition to the information about the plurality of disease lesions. Hence, the determination of the clinical information can be accelerated by using a graph representation of the plurality of disease lesions in combination with a graph machine learning model as only information which is relevant for determining the clinical information is processed. Furthermore, it is easier for the graph machine learning model to be trained properly if the provided input data does not contain too much unrelated information.

According to a further possible embodiment of the invention the graph representation of the plurality of disease lesions comprises information about a global feature of each disease lesion of the plurality of disease lesions.

In particular, a global feature of a disease lesion describes its relationship to other disease lesions or other patient organs or anatomical landmarks. Such a global feature can therefore comprise information about the spatial relationship of a given disease lesion to another disease lesion or to an anatomical landmark. In other words, connections between all or a subset of the plurality of disease lesions can be expressed by the global feature. Advantageously, a global feature of a disease lesion can describe its influence on the other disease lesions of the plurality of disease lesions and/or its influence on the surrounding anatomy. In return a global feature of a disease lesion can describe how the disease lesion is influenced by another disease lesion and/or by its position within the patient's anatomy. A global feature can be derived from imaging data of a region of interest of the patient's anatomy. In particular, the graph representation can comprise more than one global feature of each disease lesion of the plurality of disease lesions.

The relationship between each disease lesion of the plurality of disease lesions is an important parameter that can be used to predict at least one of the disease progression, the survival, and the therapy response of the patient regarding a disease specific therapy. This relationship can be expressed by a global feature of each disease lesion.

According to a further possible embodiment of the invention the global feature of a given disease lesion comprises information about its location within the patient.

In particular, the location of a given disease lesion of the plurality of disease lesions can be given with respect to an anatomical coordinate system. The anatomical coordinate system can be spanned by anatomical landmarks given by the anatomy of a patient. For example, an anatomic structure e.g. the heart, the kidney, the hip bone, the bronchial branches etc. can be landmarks to provide the anatomical coordinate system of a patient. This anatomical coordinate system is patient specific. It is independent of the position of a patient within a medical device like CT, MRT, PET, SPECT etc. Hence, uncertainties of positioning a patient within a medical device can be neglected by using an anatomical coordinate system. In other words, the anatomical coordinate system only depends on the anatomy of a particular patient. It is independent of the medical device with which the patient is measured or the room where the patient is. In particular, the anatomical coordinate system can be normalized. That means that the distance between two landmarks is normalized to a specific distance for all patients.

According to a preferred embodiment, for all patients the same landmarks can be chosen to define the anatomical coordinate system. Thus, the distances between the landmarks can be normalized for all anatomical coordinate systems of a plurality of patients. Like this, the normalized anatomical coordinate systems are comparable for different patients. According to an example embodiment of the invention, for each of the plurality of disease lesions the global feature comprises information about its location within a patient. Determining the locations of a plurality of disease lesions with respect to a normalized anatomical coordinate system, it is easier to compare the spatial distributions of a plurality of disease lesions of different patients, who are of different sizes and weights. The global feature comprising the location of a given disease lesion can be given by an absolute value of the given single disease lesion within the given coordinate system. Alternatively or additionally, the global feature comprising the location of a disease lesion can be given by a relative value of the location of a disease lesion in relation to the distance between two landmarks. Alternatively or additionally, the global feature comprising the location of a given disease lesion can be given by an absolute and/or relative distance with regard to the other disease lesions of the plurality of disease lesions and/or with regard to the landmarks spanning the anatomical coordinate system and/or with regard to organs of the patient. Alternatively or additionally the global feature of a given disease lesion can comprise any spatial relationship with regard to other disease lesions of the plurality of disease lesions and/or with regard to landmarks. Spatial relationships can comprise for example at least one of the following: angles, distances, connections via bloodstreams, nerves, and/or lymphatics etc.

In particular, in the case that the multi-focal disease in question is a tumor disease, the location of the tumor lesion can be given with respect to the position of the primarius within an anatomical coordinate system or a normalized anatomical coordinate system. The location can be given by a relative and/or an absolute distance of the disease lesion in question to the primarius. All distances can be normalized as described above within an anatomical coordinate system.

The global information comprising the location of the plurality of disease lesions has a high impact on the prediction of the survival or therapy response of the patient. It is advantageous to locate the lesions within an anatomical coordinate system in order to avoid uncertainties of the location due to variations of the positions of the patient within the medical device. Due to long acquisition times, radiation doses, etc. full-body scans of a patient for acquiring a medical image showing all disease lesions within one image should be avoided. For providing the location of a disease lesion within an anatomical coordinate system of a patient it is not necessary to image the whole patient. It is sufficient to have enough landmarks within the image of the disease lesion to determine its location. Hence, the spatial distribution of disease lesions which are spatially separated within a patient can be encoded in one graph representation without imaging the whole patient.

Thus, global features of disease lesions have an impact on the clinical information. By integrating at least one global feature for each disease lesion in the graph representation of the plurality of disease lesions the influence of the global feature is considered when determining the clinical information.

According to a further possible embodiment of the invention, the graph representation of the plurality of disease lesions comprises information about a local feature of at least one disease lesion of the plurality of disease lesions.

A local feature describes a parameter of a given disease lesion, which is independent of the local feature of another disease lesion. In particular, the local feature can for example be the size and/or the volume and/or the structure etc. of the disease lesion in question. In particular, the local feature of a given disease lesion does not provide any information about the relationship of the given disease lesion to the other disease lesions of the plurality of disease lesions. According to an example embodiment of the invention, the graph representation of the plurality of disease lesions can comprise more than one local feature for a given disease lesion. In particular, the local feature or the local features of a given disease lesion can describe all properties of the disease lesion which might be of interest for the determination of the clinical information. In particular a local feature may be provided for each disease lesion of the plurality of disease lesions.

In some cases, a local feature may not be available for all disease lesions of a plurality of disease lesions. In such cases such local feature can be included at least for a subset of the plurality of disease lesions in the graph representation. Additionally or alternatively, an arbitrary value (e.g. an average value, a neutral value, a zero-value or similar) can be included or assigned in the graph representation for a given disease lesion, for which the local feature is not available, or not necessary.

The quality of the clinical information is improved by taking at least one local feature of each of the plurality of disease lesions into account. By integrating at least one local feature for each disease lesion in the graph representation of the plurality of disease lesions the influence of the local feature is considered when determining the clinical information. In particular, the combination of local and global features of the plurality of disease lesions enhances the prediction. It is possible to combine global and local features of a plurality of disease lesions in a very effective manner by a graph representation of the plurality of disease lesions.

According to a further possible embodiment of the invention the local feature of a given disease lesion comprises a handcrafted feature and/or an automatically extracted feature, in particular a feature extracted by a deep neural network.

The local feature can be determined in particular by a skilled person respectively a physician like a radiologist, an oncologist or a pulmonologist. Alternatively, the local feature can be determined by an unlearned algorithm. An unlearned algorithm can for example be based on segmenting a disease lesion by thresholding and for example determining the number of pixels within the segmented region. Alternatively, an unlearned algorithm can be a texture-based algorithm, determining the texture of a disease lesion within a medical image. Local features determined by such a skilled person or unlearned algorithm are called handcrafted features. The skilled person or unlearned algorithm can determine handcrafted features such as radiomics and provide them as local features. Radiomics are information based on image data comprising e.g. statistical information about tissue properties, diagnosis etc. concerning the disease lesion in question. Handcrafted means that the feature is determined "by hand" by a skilled person, possibly with support by specific image analysis tools, or by an unlearned algorithm. Specific image analysis tools can be for example computer implemented tools for measuring the size of a given disease lesion or the distance between two given disease lesions or for segmenting suspicious objects within a medical image. Furthermore, a handcrafted feature can be the size, the shape or further features of a disease lesion which can be determined in a medical image.

Additionally or alternatively, a local feature can be automatically extracted. In particular it can be provided by a deep neural network. This the deep neural network is not the same as the graph machine learning model providing the clinical information. In particular, the deep neural network can be combined with the graph machine learning model. In particular, both networks can be trained in an end-to-end manner. That means, that both networks can be trained together in one step. For this purpose, the results of the deep learning network can be directly provided as input data to the graph machine learning model without any user action. The at least one local feature provided by the deep neural network can be combined with at least one global feature for each disease lesion of the plurality of disease lesions. Both the combination of the at least one local and the at least one global feature or only the at least one local feature or only the at least one global feature can serve as input for the graph machine learning model without any user action. Both networks can be trained together in a supervised manner. In this case the input data can comprise or be based on imaging data, images, or image patches of a plurality of disease lesions of a patient and the output data can be a clinical information of a patient.

Alternatively, the deep neural network and the graph machine learning model can be trained separately. In a first step the deep neural network can be trained. The input data of the trained deep neural network can comprise or be based on imaging data of a plurality of disease lesions of a patient and the output data of the trained deep neural network can be at least one local feature for each disease lesion of the plurality of disease lesions of the patient. In a second step, the output data of the trained deep neural network can be used as input data for the trained graph machine learning model. The output data of the trained graph machine learning model can be the clinical information related to any multi-focal disease.

In particular, a local feature of a given disease lesion of the plurality of disease lesions can be determined in different ways, namely by a skilled person, an unlearned algorithm and/or by a learned algorithm, e.g. a deep neural network. It is possible to combine local features determined by either approach. With this approach the advantages of both local feature determination approaches can be combined. On the one hand, the knowledge and the intuition of a skilled person in determining a handcrafted local feature of a disease lesion can be considered. On the other hand, the results of automatic extraction, e.g. with a deep neural network, can be considered. It is advantageous to combine these embodiments and aspects to describe the plurality of disease lesions by global and local features to achieve an improved result regarding the clinical information.

According to a further possible embodiment of the invention, the graph representation includes a plurality of nodes and edges connecting these nodes, wherein each node of the plurality of nodes encodes a given disease lesion of the plurality of disease lesions and comprises at least information about the local feature of the disease lesion and wherein each edge of the plurality of edges encodes an information about the global feature.

In particular, the location of each node within the graph representation of the plurality of disease lesions of a patient can correspond to the location of a corresponding disease lesion within the anatomical coordinate system or the normalized anatomical coordinate system. In other words, each disease lesion of the plurality of disease lesions of a patient can be represented by at least one node within the graph representation. According to an example embodiment of the invention, the node can be located at the center of mass of the corresponding disease lesion. According to an alternative example embodiment of the invention, a plurality of nodes can be distributed over the surface of the corresponding disease lesion. This facilitates the geometry-based analysis of the individual disease lesion. A corresponding disease lesion of a node means that the node encodes at least a local feature of the disease lesion and that the node is advantageously located at the location of the disease lesion.

Each node can encode at least one local feature of the corresponding disease lesion. This local feature can be a handcrafted local feature and/or it can be automatically extracted, e.g. by using a deep neural network. In particular, each node can comprise at least more than one local feature of the corresponding disease lesion. These local features of a corresponding disease lesion can be a combination of handcrafted local features and local features determined automatically, e.g. by a deep neural network or they can be only handcrafted features, or they can be only local features determined automatically, e.g. by a deep neural network. In particular, a node can additionally encode global information like the absolute position of the corresponding disease lesion within the anatomical coordinate system or the normalized anatomical coordinate system, and/or the distance of the corresponding disease lesion with regard to the surrounding disease lesions, and/or the distance of the corresponding disease lesion to given landmarks and/or organs. The distances can be relative distances. Advantageously, each node comprises a feature regarding the localization and/or the orientation of the corresponding disease lesion within the organ it occurs. In particular, the node encodes information whether the corresponding disease lesion is placed at the front, at the back, at the left, at the right, etc. of an organ. In other words, the node can encode information where within an organ a disease lesion of the plurality of disease lesions is located and/or how it is oriented within the organ.

The edges of the graph representation of the plurality of disease lesions are encoding an information of the global feature of each disease lesion of the plurality of disease lesions. The edges connect single nodes of the graph representation, wherein not each node has to be connected with each other node of the plurality of nodes. The edges encode the relationship between the nodes of the graph representation of the disease lesions. In particular, the edges can encode the spatial configuration of the nodes. Hence, for example an edge connecting two nodes can comprise the distance between these nodes. The distance can be an absolute distance between the nodes, or it can be a normalized distance with respect to the anatomical coordinate system. Hence, the relative distance between two nodes can be given with respect to the normalized anatomical coordinate system.

For providing improved clinical information it is preferred to combine information of global and local features. This combination can be best realized in a graph representation. A graph representation of the plurality of disease lesions on the one hand allows to combine a local and a global feature of each disease lesion. On the other hand, a graph representation is an effective form to combine all relevant features for providing clinical information. Within the graph representation no unnecessary data is encoded like in medical images which always include data regarding body parts which contain no urgent information for determining the clinical information. For this purpose, the nodes and edges of the graph representation can be encoded as matrices.

According to a further possible embodiment of the invention the clinical information comprises at least one classification information for the prediction of the disease progression, the survival or therapy response of the patient.

The classification information relates to the association of the patient with at least one of at least two categories. These categories may be for example "high risk" and "low risk", or high, intermediate and low risk, wherein risk is the probability of a certain event occurring in a certain time period, e.g. occurrence of metastasis, disease-free survival, and the like. It can further mean a category of favorable or unfavorable clinical outcome of disease, responsiveness or non-responsiveness to a given treatment or the like.

Alternatively or additionally, the clinical information can comprise a quantitative value, such as a regression value. A regression value is a continuous output variable which can describe e.g. the probability of the occurrence of a medical event, the survival time etc.

In particular, the clinical information for the prediction of the survival can comprise a prediction about the one-year-survival and/or about the estimated survival time of the patient. The one-year-survival can be provided as two class classification information (yes/no) or it can be provided as a percentage probability that the patient survives a defined time period, e.g. the next upcoming year. The survival time can be given in years. For example, the number of years the patient will survive with a probability of 90% can be provided.

Alternatively or additionally, the classification information can comprise information about a state classification of a disease lesion. The state classification of a disease lesion comprises for example information about the disease state.

The therapy response can comprise information about the response of the disease lesions with respect to a specific therapy, e.g. surgery, radiotherapy, chemotherapy and/or the combination of such therapies. In particular, the therapy response can comprise information about the percentage of disease lesions which vanished due to therapy and/or about the reduction in size of the disease lesions. In particular, the therapy response can alternatively or additionally comprise information about changes of the velocity of the spread and/or of the growth of the plurality of disease lesions. A combination of the prediction of the survival of the patient and of the therapy response of the patient helps to observe and qualify different therapies and helps a skilled person like a physician, a radiologist, an oncologist or a pulmonologist to find the best therapy in dependence of the predicted survival and/or the state of the patient and/or disease state etc.

Providing a classification information at least for the prediction of the disease progression, the survival or the therapy response of the patient helps a physician to decide how to proceed further with regard to the choice of the best therapy or with regard to palliative care.

According to a further possible embodiment of the invention the clinical information comprises at least a feature importance information regarding at least one local or global feature.

In general, the feature importance information describes which part of the input data contributes to what portions to the output data, in a given case to the clinical information. In particular, in a given case the feature importance information provides information which of the local and/or global feature, which can be comprised by the graph representation of the plurality of disease lesions, has the most influence on the clinical information. In particular, for combining a global and a local feature and/or for combining a plurality of global and local features for each disease lesion, the feature importance information can provide information about the influence of each feature on the provided clinical information. The feature importance information can be used to visualize the influences of the different features which are encoded in the graph representation of the plurality of disease lesions. In particular, the feature importance information can provide the information on which disease lesion of the plurality of disease lesions has the most impact on the clinical information.

In a preferred embodiment the feature importance information can be provided by a saliency map, also called attenuation map. A saliency map can especially be provided for a graph convolutional neural network.

It is of high interest to observe the influences of the different features on the outcome of the clinical information. In particular, this knowledge might enable a skilled person like a radiologist, an oncologist, a pulmonologist and/or other physician to attack the plurality of disease lesions at the most efficient point. For example, if a disease lesion in one specific localization causes the predicted survival of a patient to decrease it might be promising to remove such a disease lesion first before starting further therapy. Learning about such influences of different features of the plurality of disease lesions can enable the skilled person to decide for the most efficient therapy.

According to a further possible embodiment of the invention the input data comprises a temporal series of a plurality of graph representations of the plurality of disease lesions of a patient.

In particular, a plurality of disease lesions of a patient can be observed over a longer time span for example during therapy or during palliative care. This observation can be done by taking medical images for example CT, MRT, PET or SPECT images over time, e.g. in discrete time distances. During therapy medical images of the plurality of disease lesions of a patient are taken in discrete time distances to check the development of the plurality of disease lesions. Hence, these sequences of images can be used to provide a temporal series of graph representations. From each time point a graph representation of the plurality of disease lesions can be created for example comprising a global and/or a local feature with respect to the nodes and edges of the corresponding graph representation. In particular, it can comprise more than one local and/or one global feature for each disease lesion. Hence, temporal changes of the local and global feature of the plurality of disease lesions can be observed and following these observations predictions can be made. Thus, the disease-related clinical information can comprise predictions about the future development of the plurality of disease lesions. Furthermore, the influence of therapy on the plurality of disease lesions can be observed and evaluated and can be provided via the clinical information. In other words the clinical information can comprise temporal related clinical information.

The number of graph representations of such a temporal series can be variable. A temporal series of graph representations of the plurality of disease lesions has to comprise at least one graph representation. The graph machine learning model can be trained with temporal series of graph representations of a plurality of disease lesions. Nevertheless, the trained network can be used to provide the clinical information also for a temporal series comprising only one graph representation.

Providing a temporal series of graph representations of the plurality of disease lesions takes the temporal changes of the features of the disease lesions into account. The clinical information comprising temporal related clinical information can be provided. This might enable the skilled person to decide for the most effective therapy as the temporal changes might provide further information. Furthermore, knowledge about the temporal behavior of a plurality of disease lesions might help to understand disease growth and/or changes of the plurality of disease lesions. This can help to intervene in an earlier state with the best therapy, which might help to increase the patient's survival time. Considering the known temporal behavior of the plurality of disease lesions helps to predict the future development of the plurality of disease lesions.

According to an alternative embodiment of the invention the temporal development of the plurality of disease lesions can be trained by recurrent neurons. That means that the graph machine learning model can comprise recurrent neurons. Such recurrent neurons can remember what they have seen before. Thus, a temporal series of graph representations of the plurality of disease lesions can be used as input for the graph machine learning model. The recurrent neurons combine the information and can predict future temporal developments. The clinical information can comprise these future temporal developments. In this embodiment the graph machine learning model is designed as a graph neural network.

According to another alternative embodiment of the invention the changes of the disease lesions over the time are provided as a local feature of the latest graph representation in a temporal series. In other words, each node corresponding to a disease lesion of the plurality of disease lesions, for which information of earlier images is known, comprises information about the local and/or global feature of the the disease lesion at previous times. Thus, the local features of the plurality of nodes comprise temporal information of the corresponding node. For this embodiment of the invention the graph machine learning model does not need to be trained with temporal series of graph representations as the information about the temporal changes of the plurality of disease lesions is provided by the features of the latest graph representation of the plurality of disease lesions.

According to a further alternative embodiment of the invention the temporal changes of the plurality of disease lesions can be provided by a so-called change graph. The graph representation of such a change graph comprises information about all previous states of the plurality of disease lesions which are known. The graph machine learning model can be trained on such change graphs. In this way information regarding temporal changes of the plurality of disease lesions can be considered for providing the clinical information.

According to an embodiment of the invention the clinical information can comprise information about the predicted location and time of occurrence of a potential future disease lesion.

Based on the graph machine learning model predictions can be made where and when a new potential disease lesion might grow. In tumor diseases such potential future tumor lesions may be potential future metastases.

In particular, this prediction can be provided if the previous development of the plurality of disease lesions is provided to the network. The temporal behavior of the plurality of disease lesions can be analyzed by one of the aforementioned possible aspects of the invention concerning the temporal behavior of the plurality of disease lesions.

In particular, the prediction of the location and time of a potential future disease lesion can be made receiving just one graph representation of the plurality of disease lesions as input data. Alternatively, the prediction of the location and time of a potential future disease lesion can also be made receiving a temporal series of the plurality of disease lesions as input data. The clinical information can additionally comprise the probability value where and when a potential future disease lesion might start growing. The predicted location can be provided by absolute coordinates within the anatomical coordinate system respectively the normalized anatomical system. Alternatively, the predicted location can be an area within the anatomical coordinate system respectively the normalized anatomical coordinate system. This area can comprise a continuous variation of the probability of an occurrence of a potential future disease lesion. This variation can be depicted in a colored heat map which can be superposed on an image of the patient's anatomy. In particular, the clinical information can comprise the location and time of more than one potential future disease lesion.

The prediction of the location and time of a potential future disease lesion might help to provide therapies at an earlier time point. Additionally, it might help to understand how a plurality of disease lesions spreads and which paths the disease lesions are using for spreading, for example bloodstreams and lymphatics. Additionally, it might provide some information about which paths are most probably used by a disease lesion for spreading. For further disease research it is also of interest to know where the corresponding disease lesion might start growing. It might help to solve for example the following questions: Can the disease lesion start growing in each organ or does a specific type of disease lesions prefer some organs?, How long does it take until a potential future disease lesion starts to grow and how long does it take until it can be seen in medical images such as MR or CT or it can be observed in alternative ways like PET and/or SPECT?, How does the growth of a disease lesion depend on the age of the patient?, and similar questions.

Such knowledge might help to understand the mechanism of disease growth and/or disease spread and to provide better and more specific therapies. Predictive therapies which consider the predicted development of the plurality of disease lesions can be provided.

According to a further possible embodiment of the invention the graph representation comprises information about a previous disease lesion.

A previous disease lesion is a disease lesion which was present in the patient in the past, but has disappeared spontaneously or due to therapy. In particular, the previous disease lesion might have vanished due to therapy e.g. surgery, radiotherapy and/or chemotherapy or a combination thereof. The information can be comprised within the graph representation by a node which is located at the previous location of the vanished previous disease lesion. The node can comprise a local feature of the vanished previous disease lesion. The node can also comprise a global feature like the absolute location of the vanished previous disease lesion within an anatomical or normalized anatomical coordinate system or in relation to another disease lesion. The the node can comprise both a plurality of global and local features. The the node can be connected via edges with nodes which are representing still existing disease lesions. A local feature of the node representing the vanished previous disease lesion can comprise a local feature that encodes the fact that the previous disease lesion has vanished.

According to an example embodiment of the invention, more than one vanished previous disease lesion can be comprised by the graph representation. In particular, all vanished previous disease lesions can be comprised by the graph representation of the plurality of disease lesions. In particular, in the case that the multi-focal disease in question is a tumor disease, a previous tumor lesion can be the primarius or a metastasis.

Taking the influence of vanished previous disease lesions into account might improve the provided clinical information. A vanished previous disease lesion still might have some influence on the development of the plurality of disease lesions as a whole. It even might be the reason for the growth of future disease lesions, due to the time-shift between the event that initiates the growth of a future disease lesion and the start of the growth of the future disease lesion. Thus, it is advantageous to take the influence of previous disease lesions into account via a node within the graph representation of the plurality of disease lesions and via corresponding edges connecting this node with other nodes of the graph representation.

In a further embodiment of the invention the graph representation of a plurality of disease lesions comprises several subgraphs. A subgraph is a graph representation of a subset of the plurality of disease lesions.

In an example embodiment a subgraph may comprise a graph representation at a given time point in a temporal series of time points.

In a further example embodiment, a subset of disease lesions can be determined which comprises nodes which are located within one organ. Thus, for instance, the subset of the plurality of disease lesions located in the brain are represented by one subgraph, the subset of the plurality of disease lesions located in the liver form another subgraph, and so on. A subgraph can be used as input for the graph machine learning model in a similar fashion as the graph representation of all disease lesions of the plurality of disease lesions. Hence, the graph machine learning model can either provide clinical information with respect to only one of such subgraphs or it can provide clinical information based on the whole graph representation of all disease lesions of the plurality of disease lesions. The plurality of subgraphs can provide information about the full-body disease burden of the patient. For example, by combining subgraphs of all infested organs the disease burden of the patient as a whole can be analyzed. In this example, the single subgraphs allow to analyze the development of a subset of the plurality of disease lesions within one organ. The nodes or at least a subset of the nodes of the single subgraphs can be interconnected by edges. These edges can comprise information about the distance between the nodes of the different subsets. The distance can be given with respect to an anatomical coordinate system respectively a normalized anatomical coordinate system. The distances can be absolute and/or relative distances. The distances can refer to landmarks of the anatomical coordinate system respectively of the normalized anatomical coordinate system and/or they can refer to other disease lesions of the plurality of disease lesions and/or they can refer to organs of the patient. In the case that the multi-focal disease in question is a tumor disease the distances can in particular refer to distances between a given metastasis and other metastases and/or the primarius.

The subdivision of one graph representation into a plurality of subgraphs for different organs allows the analysis of both the full-body disease burden as a whole by considering the whole graph representation and of the subset of the disease lesions within one organ. The latter helps to increase efficiency in calculating the clinical information, if only the development of the subset of disease lesions within one organ is of interest. Furthermore, the subsets allow to compare for example a patient who has a plurality of disease lesions only within the brain with another patient who has a plurality of disease lesions within the brain and the liver. For this purpose, only the subset of disease lesions within the brain of the second patient can be analyzed. This holds true for all organs. Hence, even if no patients in the training data set had the same configuration of affected organs as the current patient to analyze, this patient can still be analyzed if subgraphs trained for individual organs in other patients (and their mutual connections, as far as available) are combined into a graph representation for this patient.

In a further embodiment, the invention relates to a system for providing the clinical information, comprising a first interface, configured for receiving input data, wherein the input data comprises a graph representation of a plurality of disease lesions of a patient, comprising a second interface, configured for providing the clinical information, wherein the clinical information comprises at least one information for the prediction of the disease progression, the survival, or the therapy response of the patient and comprising a computation unit, configured for applying a trained function to the input data to generate the clinical information, wherein the trained function is based on a graph machine learning model, wherein the information is generated.

In a further embodiment, the invention relates to a computer program comprising instructions which, when the program is executed by a computer system, cause the computer system to carry out the method of at least one embodiment of the invention as explained above together with its potential aspects.

In a further embodiment, the invention relates to a computer-readable medium comprising instructions which, when executed by a computer system, cause the computer system to carry out the method of at least one embodiment of the invention explained above together with its potential aspects.

In a further embodiment, the invention relates to a training system, comprising a first training interface, configured for receiving input training data, wherein the input training data comprises a graph representation of a plurality of disease lesions of a patient, a second training interface, configured for receiving output training data, wherein the input training data is related to the output training data, wherein the output draining data comprises a clinical information, wherein the clinical information comprises at least one information for the prediction of the disease progression, the survival or therapy response of the patient, a training computation unit, configured for training a function based on the input training data and the output training data, a third training interface, configured for providing the trained function.

In a further embodiment, the invention relates to a computer program comprising instructions which, when the program is executed by a training system, cause the training system to carry out the method of at least one embodiment, together with its potential aspects and embodiments.

In a further embodiment, the invention relates to a computer-readable medium comprising instructions which, when executed by a training system, cause the training system to carry out the method of at least one embodiment, together with its potential aspects and embodiments.

In FIG. 1 the computer implemented method for providing a clinical information also referred to as clinical information related to any multi-focal disease is schematically depicted. The method comprises the steps of receiving global features 107 of a plurality of disease lesions, receiving local features 105 of a plurality of disease lesion, applying the trained function of the graph machine learning model 109 and the step providing the clinical information 111. The steps of receiving local features 105 and of receiving global features 107 may be executed in any sequence.

In the step of receiving global features 107, information about the location of each single disease lesion of the plurality of disease lesions is provided to the network. The locations of the single disease lesions can be provided in relation to a normalized anatomical coordinate system. The plurality of disease lesions can comprise the disease burden of one organ or it can comprise the full-body disease burden. The locations of the plurality of disease lesions can be the locations determined within the plurality of medical image respectively image patches of the plurality of disease lesions. Alternatively, the locations can comprise a temporal series of locations of each of the plurality of disease lesions of several medical images of each disease lesion.

In the step of receiving local features 105, information about the local features of each disease lesion of the plurality of disease lesions is provided to the network. The local features can comprise for example the size, the structure the compactness etc. of the single disease lesion. The local features of the plurality of disease lesions can be the local features determined with the help of one medical image of each disease lesion. Alternatively, the local features can comprise a temporal series of local features of at least one local feature of the plurality of disease lesions.

The graph representation of the plurality of disease lesions is described by matrices which comprise the of global and local features received in steps of receiving local features 105 and of receiving global features 107. In this embodiment the first layer of the graph machine learning model is a graph construction layer. The matrices describing the graph representation are created in this graph construction layer based on the global and local features.

In step of applying the trained function of the graph machine learning model 109 the clinical information is determined. In a first step the local features of the plurality of disease lesions are arranged in a N×D matrix X. N is the number of nodes. In other words, N is the number of disease lesions within the plurality of disease lesions. D is the number of features per node. Thus, X encodes at least all features of each node. The features of a node comprise at least one local feature of each disease lesion. Advantageously, the features encoded in the matrix X also comprise a spatial information of each disease lesion. In a second step the spatial configuration of the plurality of disease lesions is encoded by a N×N matrix A by the graph construction layer. A can be called the (weighted) adjacency matrix of the graph or a function thereof. A encodes the global features of the plurality of disease lesions. A encodes how information is propagated between the nodes and thereby incorporates the global, spatial information. The first and the second step of the step of applying the trained function 109 can be executed in any sequence.

Advantageously, the graph machine learning model is a graph neural network especially a graph convolutional neural network comprising multiple layers. A single graph convolutional layer may be written as a function $$f(H^l, A) = \sigma(A H^l W^l).$$

$H^1$ holds the features of the l-th network layer, with $X = H^0$. $W^l$ is a matrix of trainable weights, which are trained during the training respectively supervised learning procedure of the graph convolutional neural network. σ is a non-linear activation function. Stacking several of these functions, while ensuring that the spectral radius of the matrix A is normalized such that the values after multiplication do not diverge, a graph machine learning model network as described above can be obtained.

After executing the graph machine learning model, the step of providing the results 111 is executed. The results are the clinical information. The clinical information can comprise a classification information for the prediction of the disease progression, the survival and/or the therapy response. Additionally, it can comprise a feature importance information, especially a saliency map, showing which of the provided features of the plurality of disease lesions contributes most to the provided clinical information. Furthermore, the clinical information can comprise information about potential future disease lesions. It can comprise information about the potential location and the potential time when the potential future disease lesions might start growing. Additional temporal related clinical information that can be comprised by the clinical information can be trained. The clinical information can be provided in a graphical manner like exemplarily shown in FIG. 5 and as further described in connection with FIG. 5 further below.

Figure 2:
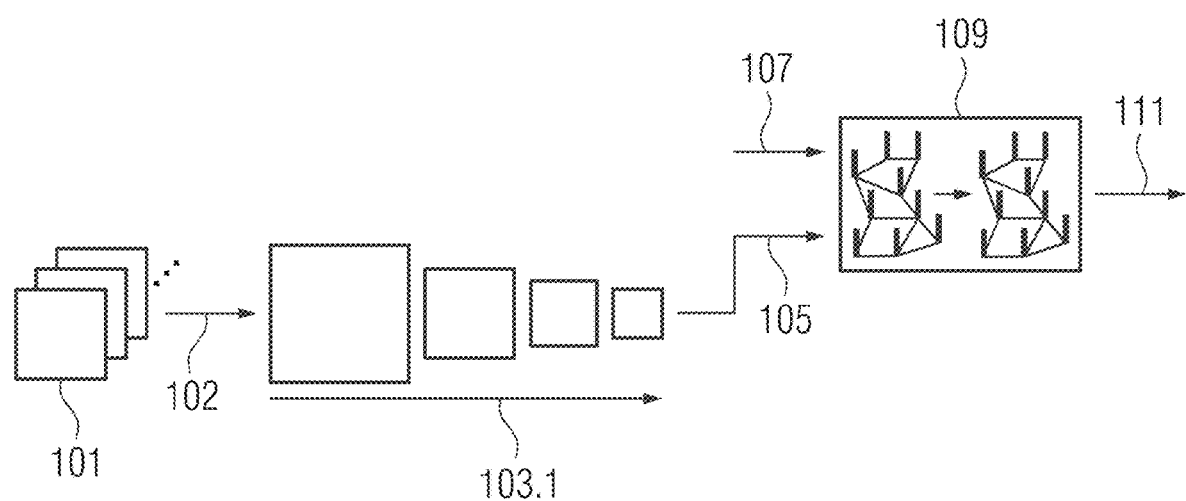
FIG. 2 shows a schematic flow chart of the method for providing a clinical information in combination with an automatically extracted local feature of a disease lesion.

In FIG. 2 the computer implemented method for providing the clinical information 111 explained in relation to FIG. 1 is shown in combination with a deep neural network for providing the local features of each of the plurality of disease lesions is shown. A plurality of patches of images 101 of the single disease lesions of the plurality of disease lesions is provided to a deep neural network in step 102. The patches do not have to have any relationship. The spatial relation between the patches is determined separately. The deep neural network is applied 103.1. Advantageously, the deep neural network is a convolutional neural network encoder. The deep neural network provides the information about the local features of the plurality of disease lesions to the graph machine learning model. The steps of receiving global features 107 of a plurality of disease lesions, receiving local features 105 of a plurality of disease lesion, applying the trained function of the graph machine learning model 109 and the step of providing 111 the clinical information are executed in analogy to the description of FIG. 1. Hereby, the local information is provided by the deep neural network to the graph machine learning model.

The deep neural network and the graph machine learning model can in one embodiment have been trained together in an end-to-end manner. In this case, the input of the supervised learning is provided to the deep neural network and the output of the supervised learning is provided by the graph machine learning model. Alternatively, the deep neural network and the graph machine learning model are trained separately. In this case, two independent supervised learning algorithms are executed for each of the both networks.

The spatial configuration of the single disease lesions is determined in a separate step with the help of image patches 101 depicting the plurality of disease lesions together with anatomical landmarks. This spatial configuration is received 107 as global features by the graph machine learning model.

Figure 3:
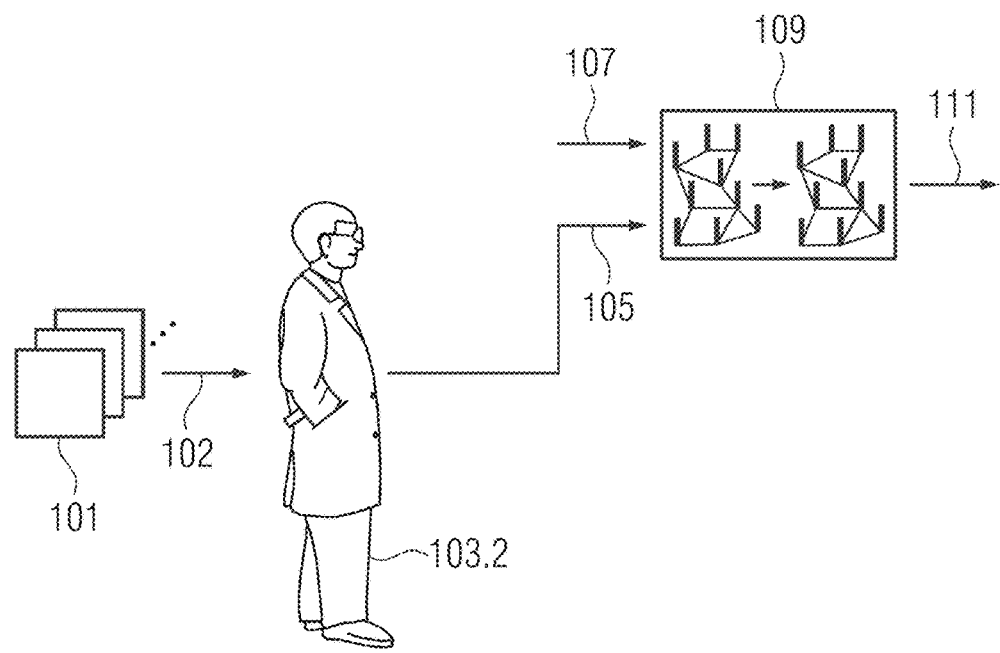
FIG. 3 shows a schematic flow chart of the method for providing a clinical information in combination with a handcrafted local feature of a disease lesion.

In FIG. 3 the computer implemented method for providing clinical information which is explained in relation to FIG. 1 is shown, in combination with an alternative approach to determine the local information. This embodiment starts by providing 102 the plurality of image patches 101 of the plurality of disease lesions to a skilled person like a radiologist, an oncologist, a pulmonologist and/or physician. The method comprises determining 103.2 handcrafted local features by eye based on the image information by the skilled person. Such a handcrafted feature can be provided via an input device or interface. In an alternative embodiment handcrafted features can be extracted by an unlearned algorithm like a texture-quantifying algorithm and/or by a segmentation algorithm. The steps of receiving global features 107 of a plurality of disease lesions, receiving local features 105 of a plurality of disease lesion, applying 109 the trained function of the graph machine learning model and the step of providing the clinical information 111 are executed in analogy to the description of FIG. 1. Hereby the local features of each of the plurality of disease lesions is provided by the skilled person to the graph machine learning model.

The spatial configuration of the single disease lesions is determined in a separate step with the help of image patches 101 depicting the plurality of disease lesions together with anatomical landmarks. This spatial configuration is received 107 as global features by the graph machine learning model.

Figure 4:
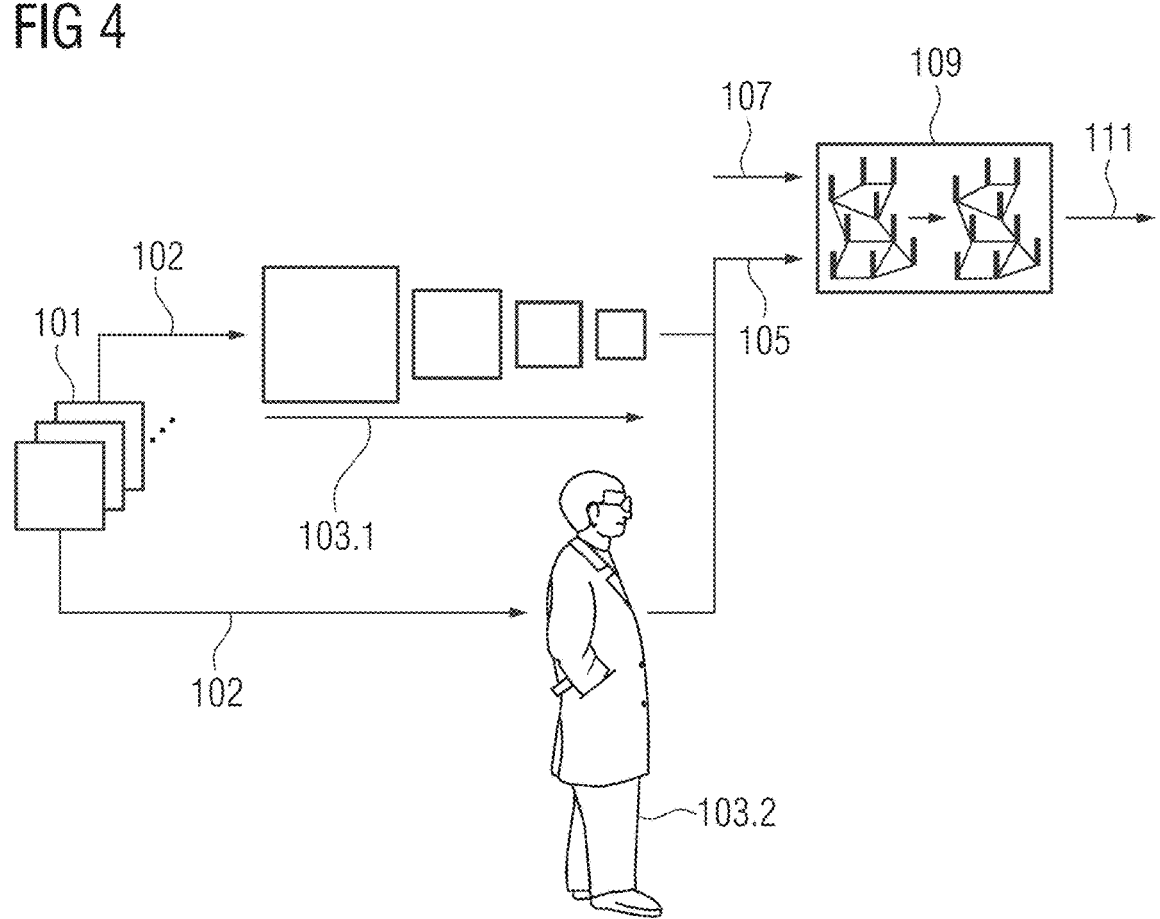
FIG. 4 shows a schematic flow chart of the method for providing a clinical information in combination with an automatically extracted and a handcrafted local feature of a disease lesion.

In FIG. 4 a combination of the embodiment shown in FIG. 2 and the embodiment shown in FIG. 3 is depicted. The image patches 101 are provided 102 to both a deep neural network and a skilled person. Both determine local features 103.1, 103.2 of each of the disease lesions of the plurality of disease lesions. These local features of both approaches are combined and are both received 105 by a graph machine learning model. In alternative embodiments a further preprocessing might be performed to ensure that the local features of a single disease lesion are in accordance with each other and do not comprise local features twice due to the combination of the two determining 103.1, 103.2 steps. The steps of receiving global features 107 of a plurality of disease lesions, receiving local features 105 of a plurality of disease lesion, applying the trained function of the graph machine learning model 109 and the step of providing the clinical information 111 are executed in analogy to the description of FIG. 1.

The spatial configuration of the single disease lesions is determined in a separate step with the help of image patches 101 depicting the plurality of disease lesions together with anatomical landmarks. This spatial configuration is received 107 as global features by the graph machine learning model.

Figure 5:
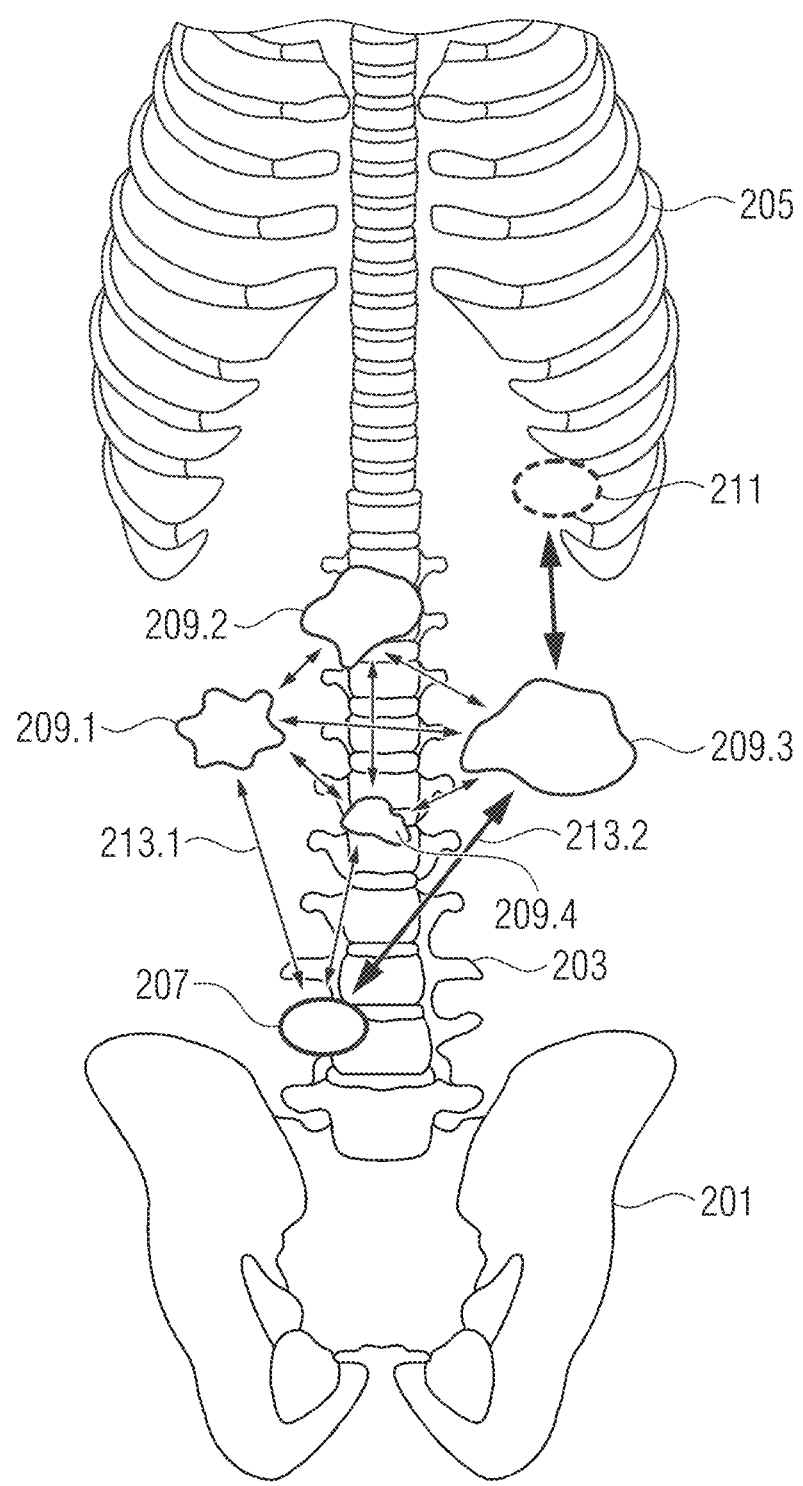
FIG. 5 shows a schematic view of the potential output of the method for providing a clinical information wherein the multi-focal disease in question is a tumor disease.

In FIG. 5 an embodiment for the graphical depiction of the provided clinical information is shown. The multi-focal disease in the example is a tumor disease. Therefore, the plurality of disease lesions in this example is a plurality of tumor lesions. The clinical information is superposed on an image of a human skeleton comprising the part or region of the human body that is infested by tumor lesions.

In the depicted embodiment the human skeleton comprises the hip bone 201, the spinal column 203 and the ribs 205. The plurality of tumor lesions 209.1, 209.2, 209.3, 209.4 is depicted within the skeleton. The single tumor lesions 209.1, 209.2, 209.3, 209.4 are located at the correct location within the anatomical coordinate system spanned by the human skeleton. Advantageously, the depiction of the single tumor lesions 209.1, 209.2, 209.3, 209.4 additionally shows the size and the structure of the corresponding tumor lesion 209.1, 209.2, 209.3, 209.4 in the image provided to the user. The depiction of the plurality of tumor lesions 209.1, 209.2, 209.3, 209.4 might be a segmented representation of the tumor lesions 209.1, 209.2, 209.3, 209.4 within the image patches 101.

The image patches 101 are provided 102 as input data to the deep neural network and/or to the skilled person. The global features of the plurality of tumor lesions 209.1, 209.2, 209.3, 209.4 are for example depicted by the location of each single tumor lesion 209.1, 209.2, 209.3, 209.4 in relation to the human skeleton. Additionally, the global features are expressed by interconnections 213.1, 213.2 between the single tumor lesions 209.1, 209.2, 209.3, 209.4. These interconnections 213.1, 213.2 are represented by arrows. For clarity only two interconnections 213.1, 213.2 are indicated by a reference numeral.

The output of the saliency map is depicted by the size and thickness of the interconnection 213.1, 213.2. The thicker an interconnection 213.1, 213.2 the more influence the corresponding interconnection has on the provided clinical information. In an alternative embodiment, the saliency map with respect to the local features can be depicted by a colour coded heatmap which is superposed over the human skeleton (not shown in FIG. 5). It can be coloured red around tumor lesions 209.1, 209.2, 209.3, 209.4 that have a high influence on the clinical information and blue around tumor lesions 209.1, 209.2, 209.3, 209.4 that have less influence in the clinical information.

The primarius 207 already vanished due to a surgery in this example. Nevertheless, it is depicted by a solid circle which is located at the former location of the primarius 207. Other vanished previous tumor lesions can be depicted in the same manner. Predicted potential future tumor lesions 211 are depicted by dashed circles at the predicted location. The solid circles of already vanished previous tumor lesions in this embodiment the primarius 207 and the dashed circles of potential future tumor 211 lesions can be different colours. These circles can be interconnected with the other tumor lesions 209.1, 209.2, 209.3, 209.4 by interconnections 213.1, 213.2 which encode the global information.

Further clinical information regarding a given tumor lesion of the plurality of tumor lesions 209.1, 209.2, 209.3, 209.4 including previous tumor lesions 207 and potential future tumor lesions 211, can be provided by for example clicking onto the given tumor lesion in question. Then a further window can pop up showing further clinical information regarding the tumor lesion in question. The clinical information can comprise the local features and/or predicted information about any of the tumor lesions 207, 211, 209.1, 209.2, 209.3, 209.4. The predicted information for example can comprise information about the predicted start time of growth of a potential future tumor lesion 211.

Furthermore, general disease-related clinical information like information for the prediction of the disease progression, the survival or therapy response can be displayed in further windows.

The graphical depiction of clinical information of other multi-focal diseases can be based on the same principle.

Figure 6:
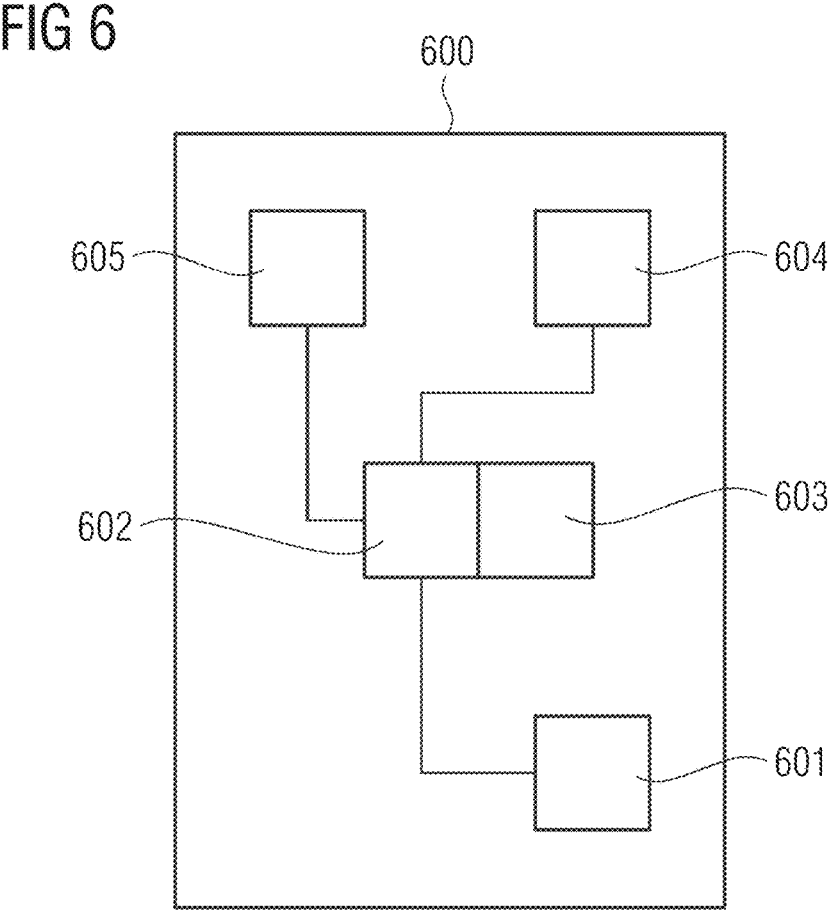
FIG. 6 shows a schematic view of the system for providing a clinical information.

In FIG. 6 the system 600 for providing a disease-related clinical information is schematically depicted. The system 600 comprises devices, like a central processing unit, a storage etc., arranged and configured to execute at least the steps 105 to 111 of the method of FIGS. 1 to 4. The system 600 is a data processing system and may be implemented in a personal computer (PC), a laptop, a tablet, a server, a distributed system (e.g. cloud system) and the like. The data processing system 600 comprises a central processing unit (CPU) 601, a memory having a random access memory (RAM) 602 and a non-volatile memory (MEM, e.g. hard disk) 603, a human interface device (HID, e.g. keyboard, mouse, touchscreen etc.) 604 and an output device (MON, e.g. monitor, printer, speaker, etc.) 605. The CPU 601, RAM 602, HID 604 and MON 605 are communicatively connected via a data bus. The RAM 602 and MEM 603 are communicatively connected via another data bus.

The method according to the first embodiment of the present invention and schematically depicted in FIGS. 1 to 4 can be loaded in form of a computer program into the RAM 602 rom the MEM 603 or another computer-readable medium having stored the respective computer program. According to the computer program the CPU executes at least the steps 105 to 111 of the method of FIGS. 1 to 4. The execution can be initiated and controlled by a user (e.g. practitioner/radiologist/oncologist/skilled person) via the HID 604.

The status and/or result of the executed computer program may be indicated to the user by the MON 605. The results of the executed computer program (disease-related clinical information) may be permanently stored on the non-volatile MEM 603 or another computer-readable medium. The disease-related clinical information which is based on image patches 101 of a clinical examination (e.g. different types of CT/MRI/PET/SPECT/sonography examination) for given clinical questions is determined and stored in the MEM 603. The optimal clinical examination for a given clinical question is automatically selected by the system 600 and may be output by the MON 605 and/or stored in the MEM 603.

Figure 7:
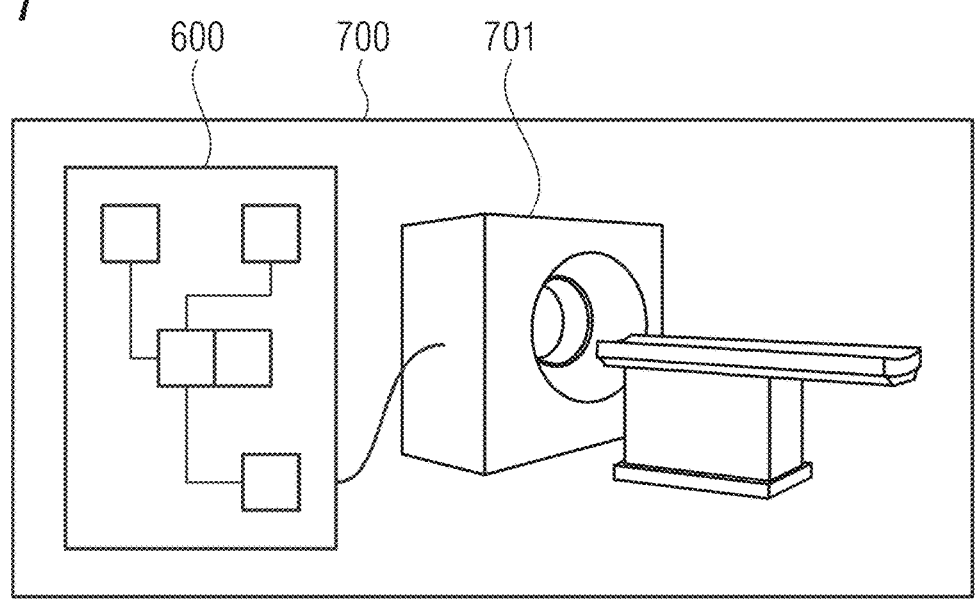
FIG. 7 shows a schematic view of the system comprising the providing system for a clinical information.

In FIG. 7 the medical imaging system 700 comprising the system 600 of FIG. 6 arranged and configured to execute at least the steps 105 to 111 of the method of FIGS. 1 to 4 is schematically depicted. The medical imaging system comprises devices for conducting a medical imaging examination like CT, MRI, PET, SPECT and/or sonography examination. Here, as an example, the medical imaging system comprises a CT scanner 701 arranged and configured to conduct at least CT examinations. The CT scanner 701 is communicatively coupled to the system 600 and can receive the clinical examination (here type of CT examination) that has been selected based on the value for the clinical examination by the system 600. Based on the stored values of clinical examinations (e.g. different types of CT/MRI/PET/SPECT/sonography examination) for a given clinical question, which have been derived and stored by the system 600, the optimal clinical examination for the given clinical question is automatically selected and communicated to the CT scanner 701.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A computer-implemented method for providing clinical information, the computer-implemented method comprising:
    receiving input data, the input data including a graph representation of a plurality of disease lesions of a patient, the graph representation including a plurality of nodes and a plurality of edges connecting the plurality of nodes, the plurality of nodes encoding the plurality of disease lesions;
    applying a trained function to the input data to generate the clinical information, the trained function being based on a graph machine learning model; and
    providing the clinical information, the clinical information including information for prediction of at least one of disease progression, survival, or therapy response of the patient.

2. The computer-implemented method of claim 1, wherein the graph representation of the plurality of disease lesions includes information about a global feature of each disease lesion of the plurality of disease lesions.

3. The computer-implemented method of claim 2, wherein the global feature of a respective disease lesion, of the plurality of disease lesions, includes information about a respective location within the patient.

4. The computer-implemented method of claim 2, wherein the graph representation of the plurality of disease lesions includes information about a local feature of at least one disease lesion of the plurality of disease lesions.

5. The computer-implemented method of claim 4, wherein the local feature of a respective disease lesion, of the plurality of disease lesions, includes at least one of a handcrafted feature and an automatically extracted feature.

6. The computer-implemented method of claim 4, wherein each node of the plurality of nodes encodes a respective disease lesion of the plurality of disease lesions and includes at least the information about the local feature of the respective disease lesion and wherein each edge of the plurality of edges encodes information about the global feature.

7. The computer-implemented method of claim 1, wherein the clinical information includes classification information for at least one of the disease progression, the prediction of the survival or therapy response of the patient.

8. The computer-implemented method of claim 1, wherein the clinical information includes at least a feature importance information regarding at least one local or global feature.

9. The computer-implemented method of claim 1, wherein the input data includes a temporal series of a plurality of graph representations of the plurality of disease lesions of the patient.

10. The computer-implemented method of claim 1, wherein the clinical information includes information about at least one of predicted location or predicted time of occurrence of a potential future disease lesion.

11. The computer-implemented method of claim 1, wherein the graph representation includes information about a previous disease lesion.

12. The computer-implemented method of claim 3, wherein the graph representation of the plurality of disease lesions includes information about a local feature of at least one disease lesion of the plurality of disease lesions.

13. The computer-implemented method of claim 12, wherein the local feature of a respective disease lesion, of the plurality of disease lesions, includes at least one of a handcrafted feature or an automatically extracted feature.

14. The computer-implemented method of claim 5, wherein each node of the plurality of nodes encodes a respective disease lesion of the plurality of disease lesions and includes at least the information about the local feature of the respective disease lesion and wherein each edge of the plurality of edges encodes information about the global feature.

15. The computer-implemented method of claim 1, wherein the trained function includes a neural network.

16. A system for providing clinical information, the system comprising:

a first interface configured to receive input data, the input data including a graph representation of a plurality of disease lesions of a patient, the graph representation including a plurality of nodes and a plurality of edges connecting the plurality of nodes, the plurality of nodes encoding the plurality of disease lesions;

a second interface configured to provide the clinical information, the clinical information including information for prediction of at least one of disease progression, survival, or therapy response of the patient; and at least one processor configured to apply a trained function to the input data to generate the clinical information, the trained function being based on a graph machine learning model.

17. The system of claim 16, wherein the graph representation of the plurality of disease lesions includes information about a global feature of each disease lesion of the plurality of disease lesions.

18. A non-transitory computer program product, storing a program including instructions which, when the program is executed by a computer system, cause the computer system to carry out the method of claim 1.

19. A non-transitory computer-readable medium storing instructions which, when executed by a computer system, cause the computer system to carry out the method of claim 1.

20. A training system, comprising a first training interface configured to receive input training data, the input training data including a graph representation of a plurality of disease lesions of a patient, the graph representation including a plurality of nodes and a plurality of edges connecting the plurality of nodes, the plurality of nodes encoding the plurality of disease lesions;

a second training interface configured to receive output training data, the input training data being related to the output training data and the output training data including clinical information, the clinical information including information for prediction of at least one of disease progression, survival, or therapy response of the patient;

at least one processor configured to train a function based on the input training data and the output training data; and a third training interface configured to provide the trained function.

21. The training system of claim 20, wherein the graph representation of the plurality of disease lesions includes information about a global feature of each disease lesion of the plurality of disease lesions.

* * * * *